(12) United States Patent
Illemann et al.

(10) Patent No.: US 10,983,072 B2
(45) Date of Patent: Apr. 20, 2021

(54) METHOD FOR DIMENSIONAL X-RAY MEASUREMENT, IN PARTICULAR BY COMPUTED TOMOGRAPHY, AND X-RAY COMPUTED TOMOGRAPHY SCANNER

(71) Applicant: BUNDESREPUBLIK DEUTSCHLAND, vertreten durch das BUNDESMINISTERIUM FÜR WIRTSCHAFT UND ENERGIE, dieses vertreten durch den PRÄSIDENTEN DER PHYSIKALISCH-TECHNISCHEN BUNDESANSTALT, Braunschweig (DE)

(72) Inventors: Jens Illemann, Braunschweig (DE); Markus Bartscher, Edemissen (DE)

(73) Assignee: BUNDESREPUBLIK DEUTSCHLAND, VERTRETEN DURCH DAS BUNDESMINISTERIUM FUR WIRTSCHAFT UND ENERGIE, DIESES VERTRETEN DURCH DEN PRASIDENTEN DER PHYSIKALISCH-TECHNISCHEN BUNDESANSTALT, Braunschweig (DE)

(*) Notice: Subject to any disclaimer, the term of this patent is extended or adjusted under 35 U.S.C. 154(b) by 0 days.

(21) Appl. No.: 16/481,582

(22) PCT Filed: Feb. 2, 2018

(86) PCT No.: PCT/EP2018/052686
§ 371 (c)(1),
(2) Date: Jul. 29, 2019

(87) PCT Pub. No.: WO2018/141917
PCT Pub. Date: Aug. 9, 2018

(65) Prior Publication Data
US 2020/0003704 A1 Jan. 2, 2020

(30) Foreign Application Priority Data

Feb. 6, 2017 (DE) .................... 10 2017 102 254.6

(51) Int. Cl.
*G01N 23/04* (2018.01)
*G06T 5/00* (2006.01)
(Continued)

(52) U.S. Cl.
CPC .......... *G01N 23/046* (2013.01); *A61B 6/582* (2013.01); *G06T 5/001* (2013.01); *G06T 11/005* (2013.01); *G01N 2223/3306* (2013.01)

(58) Field of Classification Search
CPC ................ A61B 6/582; G01N 23/046; G01N 2223/3306; G06T 11/005; G06T 2207/10081; G06T 2207/30108
See application file for complete search history.

(56) References Cited

U.S. PATENT DOCUMENTS

| 8,208,603 B2 | 6/2012 | Sato |
| 2006/0058974 A1 | 3/2006 | Lasiuk et al. |

(Continued)

FOREIGN PATENT DOCUMENTS

EP 2 644 095 A1 10/2013

OTHER PUBLICATIONS

Oliveira et al: "Characterization and Correction of Geometric Errors Induced by Thermal Drift in CT Measurements", Key Engineering Materials, vol. 613, pp. 327-334, May 21, 2014.
(Continued)

*Primary Examiner* — Mark R Gaworecki
(74) *Attorney, Agent, or Firm* — W&C IP

(57) ABSTRACT

The invention relates to a method for dimensional measurement by way of X-ray computed tomography, featuring the steps (a) Irradiating a test object (26) with non-monochro-
(Continued)

Figure 1:
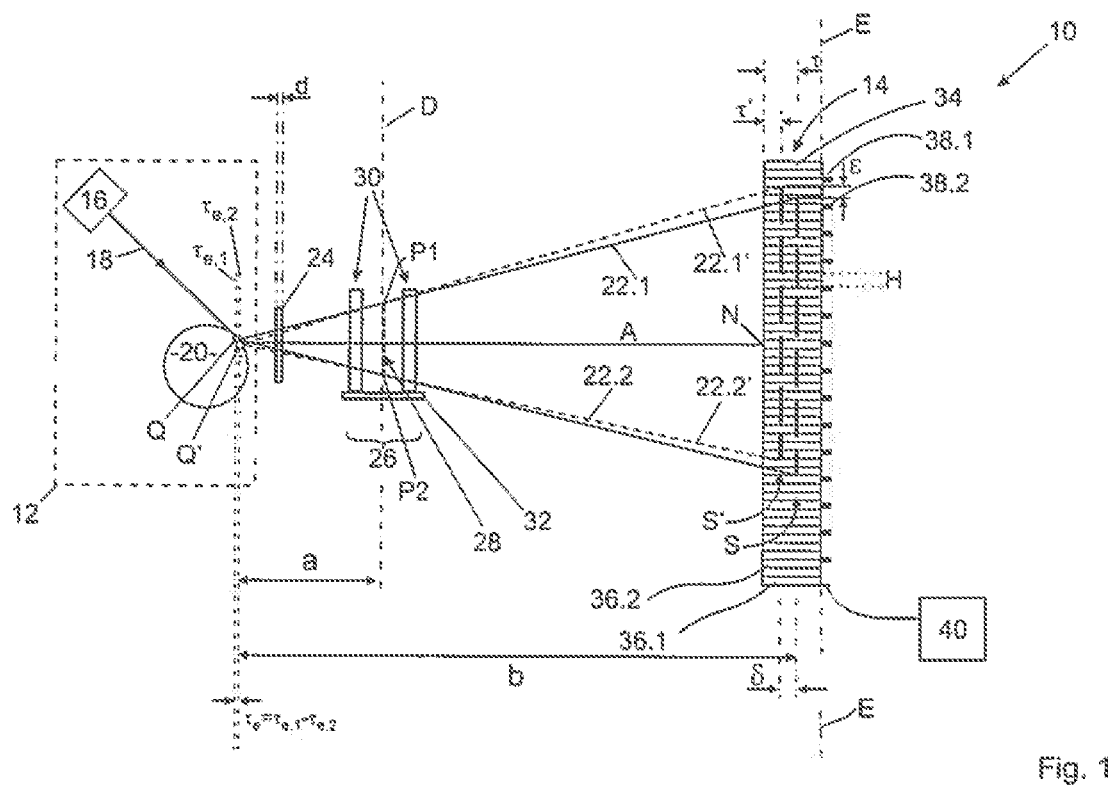

matic X-ray radiation from a virtually punctiform X-ray source (12), (b) measuring the intensity (I) of the X-ray radiation (22) in the radiation path behind the test object (26) by means of a detector (14) which has a plurality of pixels (P) to obtain pixel-dependent intensity data (I(P)), and (c) calculating at least one dimension (H) of the test object (26) using the pixel-dependent intensity data (I(P)). According to the invention, the pixel-dependent intensity data (I(P)) is corrected by the influence of an effective penetration depth ($\tau$) on the detector and/or a displacement of the effective source location (Q) on a target (20) of the X-ray source (12).

12 Claims, 4 Drawing Sheets

(51) Int. Cl.
*G06T 11/00* (2006.01)
*A61B 6/00* (2006.01)
*G01N 23/046* (2018.01)

(56) References Cited

U.S. PATENT DOCUMENTS

| | | | |
|---|---|---|---|
| 2010/0098209 A1 | 4/2010 | Forthmann et al. | |
| 2013/0121553 A1* | 5/2013 | Thibault | G06T 11/006 382/131 |
| 2013/0259347 A1* | 10/2013 | Schmitt | G01N 23/046 382/131 |
| 2014/0003573 A1* | 1/2014 | Sadaoka | G01N 23/046 378/20 |
| 2016/0296183 A1* | 10/2016 | Flohr | A61B 6/5211 |

OTHER PUBLICATIONS

Sharma et al: "Depth-of-interaction estimates in pixelated scintillator sensors using Monte Carlo techniques", Nuclear Instruments and Methods in Physics Research A, vol. 341, pp. 117-123, 2017.
Illemann et al: "X-ray spectrum dependence of the magnification of cone-beam CT", 7th Conference of Industrial Computed Tomography, pp. 1-12, 2017.

* cited by examiner

METHOD FOR DIMENSIONAL X-RAY MEASUREMENT, IN PARTICULAR BY COMPUTED TOMOGRAPHY, AND X-RAY COMPUTED TOMOGRAPHY SCANNER

The invention relates to a method for dimensional measurement by way of computed tomography, featuring the steps (a) irradiating a test object with non-monochromatic X-ray radiation from a virtually punctiform X-ray source (b) measuring the intensity of the X-ray radiation in the radiation path behind the test object by means of a detector which has a plurality of pixels to obtain pixel-dependent intensity data, and (c) calculating at least one dimension of the test object using the pixel-dependent intensity data.

According to a second aspect, the invention relates to an X-ray computed tomography scanner with (a) an X-ray source for generating X-ray radiation, (b) a detector which has a plurality of pixels for measuring pixel-dependent intensity data of the X-ray radiation, (c) a movement device, especially a rotation device, for moving a test object, and (d) an evaluation unit for calculating a three-dimensional image of the test object using the pixel-related intensity data.

Radiography describes the method in which a test object is irradiated with X-ray radiation and the intensity of the radiation in the radiation path behind the test object is measured as an image. Computed tomography represents an expansion for deter-mining a three-dimensional image by way of the rotation and, where applicable, the movement of the test object relative to the detector and the X-ray radiation source. The three-dimensional volume image is calculated from the images at the various angular positions—the projections—by means of complex mathematical methods. In industrial computed tomography, microfocus X-ray sources and flat panel detectors are preferably used. The relative measurement uncertainty in the determination of measurements is thus currently restricted to $1\times10^{-4}$, as is shown in international comparative measurements. A lower degree of measurement uncertainty is desirable.

The disadvantages of industrial computer tomography stem from the fact that the X-ray sources used emit broadband bremsstrahlung and characteristic radiation, i.e. non-monochromatic X-ray radiation. In addition, with the given source spot diameter, the maximum radiation output is restricted. It would indeed be possible to use, for example, a synchrotron radiation source or a free-electron laser, which do not bring such disadvantages; however, this would require a dedicated major research facility that could not be used for industrial measuring tasks during routine operation.

The invention refers to the use of non-monochromatic X-ray radiation. The use of the invention preferably enables the achievement of results, almost like those achieved when using monochromatic X-ray radiation. To date, a strong pre-filtering of the X-ray radiation has been used as a practical measure in order to reduce the bandwidth of the spectrum at the expense of a lower intensity of X-ray radiation. This is contradictory to the fact that industrial computer tomography also generally requires short measuring times in order to be economical. The method according to the invention can allow for a lower pre-filtering, thereby reducing the measuring time and rendering the process more economical. The invention also aims to reduce the measurement uncertainty in computed tomography, in particular in industrial computed tomography, which is systematically adversely affected by the large bandwidth of the X-ray source.

From the article entitled "Einfluss der Quellbewegung auf Reproduzierbarkeit und Antastabweichungen im Röntgen-Computertomografen" von Weiss et al.: Conference on Industrial Computed Tomography, Wels, Austria, 2010, it is known that the thermal expansion of the target due to its being bombarded with electrons may lead to a displacement of the focal point. The article describes that a change in the operating parameters, such as acceleration voltage and beam current, due to the increase in temperature and the accompanying movement of the source location may lead to errors, whereas in the case examined beam hardening, artifacts produced by reconstruction or unknown effects are irrelevant.

The article "Depth-of-interaction estimates in pixelated scintillator sensors using Monte Carlo techniques" by Sharma et al. in "Nuclear Instruments and Methods in Physics Research A 841" (2017), pages 117-123, describes how the optical paths of photons in the scintillator detector depend on parameters such as surface roughness and absorption on the surface and the solid object. Here, it is assumed that the total energy of a photon is emitted during the first scattering event; there is also no modeling of Compton scattering. It does not describe the effect that, in the event of a diagonally incoming beam, different, non-symmetrical intensities occur on adjacent pixels—regardless of the spectral hardening of the beam.

U.S. Pat. No. 8,208,603 B2 describes how the anode angle effects the spectrum and the distribution of intensity of a useful X-ray radiation cone of an X-ray tube, and how this effect can be corrected. The effect of beam hardening on a change in the effective penetration depth or the effective source location is not described.

The invention aims to reduce the degree of measurement uncertainty in computed tomography (CT), in particular industrial computed tomography.

The invention solves the problem by way of a method according to the preamble, in which the pixel-dependent intensity data is corrected by the influence of a beam hardening-related change in the penetration depth on the detector and/or of a beam hardening-related displacement of the effective source location on a target of the X-ray source.

According to a second aspect, the invention solves the problem by way of an X-ray computed tomography scanner, the evaluation unit of which is designed to automatically conduct a method according to the invention.

The invention is based on the insight that when taking an X-ray measurement—especially in cone beam geometry—with a wide spectrum, the grayscale value of one pixel, which is determined by the absorption by the test object, has an influence on an adjacent pixel of the detector due to the physical properties of the source and the detector; this is not the case with virtually parallel and/or monochromatic X-ray radiation. The resulting local change in the scaling in the radiographic image affects a re-constructed CT image, i.e. a three-dimensional density image of the test object, which is calculated using the pixel-dependent intensity data for different orientations of the test object relative to the X-ray source and the detector. The density image is used to calculate the test object surfaces and to determine the dimensions which are eventually altered by the influence of one pixel on an adjacent pixel in the grayscale image. The local radiographic enlargement factor is determined by taking the quotient of the distance from the effective source point to the effective detection location as a numerator and the distance between the effective source point and the test object as a denominator. Here, the location of the test object in the CT is determined by the position of the rotational axis; the effective source point and detection location are determined by the expected value of the absorption or emission averaged across the spectrum absorbed in the test object on its way from the source point to the detection location.

It is known that broadband X-ray radiation exhibits beam hardening when penetrating the test object. This should be understood as the phenomenon that X-ray radiation that has a higher degree of energy and thus a shorter wavelength is generally less strongly absorbed than X-ray radiation with a lower degree of energy and thus a longer wavelength. As a result, the X-ray spectrum changes with a relative increase in the proportion of "harder", i.e. high-energy, photons.

The inventors recognized that the stronger the absorption of the X-ray radiation in the test object, the greater the effective penetration depth of the X-ray radiation in the detector. This effect is irrelevant as long as the X-ray beam strikes the detector vertically. If the detector is thus bent such that a central point of a circle of curvature corresponds with the source point of the X-ray source, this effect does not result in any measurement errors.

However, curved planar detectors are difficult to produce and are thus generally not used. This means that, at points where the X-ray beam strikes the detector at an angle other than 90°, the X-ray photons are detected on average further out the harder the X-ray radiation.

The invention can preferably be combined with known beam hardening correction, in which its grayscale values are corrected pixel-by-pixel using a non-linear function, in order to take into account the deviation of the exponential weakening of the intensity effected by the absorber thickness, known as Beer's Law. By applying the correction according to the invention in addition to known beam hardening correction, the radiographic image corresponds more accurately with the image that an ideal, i.e. very thin, detector would have measured at a given source-to-detector distance; however, a very thin detector does not have the sufficient absorption capacity for X-ray radiation. This reduces measurement uncertainty.

A further advantage is that this correction is mathematically simple and can therefore be conducted quickly without having to provide considerable computing capacity.

A further advantage is that the calculation of the three-dimensional model can be conducted using the corrected pixel-dependent intensity data in the same way as uncorrected pixel-dependent intensity data. In other words, existing software can be used.

It is also advantageous that the measuring time can be reduced due to the fact that, as described above, a strong pre-filtering of the X-ray radiation is not necessary. Due to the correction of the effective penetration depth on the detector and/or of a displacement of the effective source location, it is possible to use X-ray radiation with a greater spectral width. In other words, in comparison with previous measurement strategies, a weaker pre-filter can be used, or even no pre-filter at all. This reduces the measuring time.

It is also an advantage that larger test objects can be measured. With a typical acceleration voltage of U=225 kilovolts, it is possible to reasonably conduct a dimensional measurement of test objects with a maximum material thickness of 75 millimeters if they are made of aluminium, or with a maximum material thickness of 15 millimeters if they are made of steel. These thicknesses correspond to a 95% absorption rate if the radiation has been pre-filtered with 2 mm of copper. It has been empirically established that measurement uncertainty already increases at an absorption rate of over 50%, without the cause of this effect having been accurately identified. Given that the influence of the dependency of the spectrum on source and detector position, which effect a local change in the casting of shadows, is now known and can be corrected, greater rates of absorption can be tolerated. In other words, test objects with greater dimensions can be dimensionally measured.

The correction according to the invention renders possible a relative distance measurement uncertainty of below $3 \times 10^{-5}$. In particular, for objects that are easily deformed, such as plastic products, this measurement uncertainty lies within the measurement range that is also achieved through tactile measurements. It can therefore be reasonably expected that computed tomography based on the invention can re-place tactile measurements to a greater extent in the future.

In addition to the aspect described above that beam hardening in the test object and pre-filter effects the position of the shadow image in the detector material, a further aspect, to be understood in geometric terms, contributes to systematic measurement uncertainty. If an X-ray beam strikes the detector, said beam having been considerably weakened, i.e. hardened, its photons therefore have on average more energy, as explained above. This in turn means that the photons are more likely to originate from a source location on the target that is located close to the entry point of the electron beam on the surface, as the electrons exhibit a particularly high degree of kinetic energy at this point.

Correspondingly, the photons that strike the detector at a point where a high intensity is measured are relatively more likely to originate from a point on the target at which the electrons had a low degree of energy. For instance, this may be a lower point below the surface of the target. If the location of origin of the X-ray radiation is approximated as a point, the position of this point, and therefore the distance between this point and the detector on the one hand as well as the distance between this point and the test object on the other, depends on the intensity measured in the detector. The correction of this influence on the radiographic image and thereby the reduction in measurement uncertainty is an independent subject of the invention and also favors a preferred manifestation of the aspect of the invention described above. In other words, the displacement of the effective source location is corrected.

Within the scope of the present description, the use of an indefinite article always means that either precisely one of several of the respective objects are available. In this way, it may be that precisely one point source is available, but also two or more point sources.

A point source should be understood particularly to mean an X-ray source, wherein the source location of the X-ray radiation can be deemed, to a sufficiently good approximation, to be punctiform. This should be understood especially to mean that this approximation leads to a maximum systematic measurement uncertainty of $10^{-5}$. Specifically, when striking a target of the X-ray source, the electron beam has a maximum diameter (diameter at half the maximum value) of 0.5 millimeters, especially 0.1 millimeters. The X-ray radiation is preferably in the form of a cone beam or a fan beam.

Computed tomography should also be understood especially to mean laminography.

The term dimension should also be understood particularly to mean a geometric measurement or a geometric characteristic.

The X-ray radiation is non-monochromatic. It preferably refers to bremsstrahlung with a proportion of characteristic radiation of the target material. It is beneficial if the X-ray radiation is generated by way of irradiation of a target with electrons, wherein a degree of energy of the electrons preferably lies between 20 and 600 kiloelectronvolts, preferably between 60 and 225 kiloelectronvolts.

A movement of the test object relative to the X-ray source should be understood to mean a movement of the test object when the X-ray source does not move, a movement of the X-ray source when the test object does not move, or a movement of both.

The characteristic that the pixel-dependent intensity data is corrected for the influence of an effective penetration depth on the detector should be understood especially to mean that a change in the effective penetration depth—caused by beam hardening—is corrected. This should be understood especially to mean that the intensity data is changed in such a way that the effect that the intensity measured by a pixel positively correlates to the effective penetration depth, i.e. that a high intensity is indicative of a high effective penetration depth, is corrected.

The characteristic that the displacement of the effective source location on a target of the X-ray source is corrected should be understood particularly to mean that the displacement of the effective source location, which is caused by beam hardening, is corrected.

The detector is preferably a scintillator detector or a volume-absorbent semiconductor detector. It is favorable if said detector comprises microcolumns made of scintillating material. The scintillating material is made up thallium-doped cesium iodide or contains a gadolinium, tungsten and/or lanthanum compound.

A thickness of a detector layer, especially the height of the microcolumns, is preferably at least 400 micrometers, especially at least 500 micrometers. In this case, the influence of the spectrum dependency of the effective penetration depth of the shadow image of the test object is particularly large.

The pixel-dependent intensity data is preferably corrected by the influence of a change in the effective penetration depth on the detector (14), said change being caused by beam hardening. Alternatively or additionally, the displacement of the effective source location on a target of the X-ray source is corrected, said displacement having been caused by beam hardening.

However, the displacement of the source location is generally not only caused by beam hardening. A displacement of the source location also results from the combination of the influence of beam hardening and the spectrally variable X-ray emissions across the path of the radiation-generating electron beam in the X-ray target. This influence is preferably also corrected for.

According to a preferred embodiment, the method according to the invention comprises the following steps: for at least a majority of the pixels, especially all pixels, (i) identifying a zero point distance of the pixel from an optical axis, (ii) identifying the intensity of the X-ray radiation measured by the pixel, (iii) allocating a corrected position depending on the zero point distance and the intensity, and (iv) calculating corrected pixel-dependent intensity data from all corrected positions and the corresponding Intensities. This corrected pixel-dependent intensity data is then used to calculate, for instance, a three-dimensional model of the test object. Specifically, this calculation is no different to a method known from the prior art.

It should be noted that the identification of the intensity of the X-ray radiation measured by the pixel also comprises the identification of the intensity of the absorbed X-ray radiation measured by the pixel.

The optical axis should be understood especially to mean the line along which an imagined X-ray beam runs from the X-ray source to the detector, wherein this X-ray beam runs vertically to a detector surface, along which the detector extends.

The effective source and detector displacement, which is determined by the absorption spectrum, does not have an influence on the detected position of an imagined X-ray beam in relation to a detector pixel, as long as the relevant pixel lies on the optical axis. The greater the distance of a pixel from the optical axis, the greater the deviation of the measurement location caused by the displacements.

Both corrections, namely of the source location and the penetration depth in the detector, may differ in different ranges of the intensity data.

The identification of the intensity should be understood especially to mean that a measured value is recorded that describes the intensity of the X-ray radiation. For instance, an intensity identified in this way may refer to a grayscale value that codifies the intensity measured by the corresponding pixel.

The correction of the pixel-dependent intensity data is preferably conducted such that the corrected position, the zero point and the original position of the corresponding pixel lie on one line. The zero point is the point on the detector where the distance from the optical axis is zero. In other words, if the detector is considered in a polar coordination system, the correction by the influence of the penetration depth does change the distance coordinates but not the azimuthal angle.

In order to compensate the effect of the effective displacement of the source and/or detector location for each pixel, the impact of the effect with negative signs is applied to the image in such a way that a differential distance $\Delta r$ between the zero point distance of the corrected position and the zero point distance of the uncorrected position r is generally calculated from a product of the distance r, the absorbed intensity ($I_0$–I) measured by the respective pixel and an intensity correction parameter k, and a constant c that is dependent on the filter and test object material: $\Delta r = r*((I_0-I)*k+c)$.

A radial displacement of the pixel proportional to the distance r describes a change in the geometric enlargement factor of an industrial CT with a point source and flat panel detector. The constant c describes a change in the enlargement for the entire image by way of the position of the absorption image of a thin layer of the test object in the detector. This depends of the spectrum of the X-ray source, i.e. in particular acceleration voltage, target material, filter material and thickness. This intensity correction parameter k depends on the test object material, the source conditions, especially acceleration voltage and target material, and the detector, especially material and thickness.

Conversely, the intensity correction parameter does not depend on the zero point distance r itself, at least in a linear order of the zero point distance. In particular, the intensity correction parameter does not depend, to a good approximation, on the intensity, as experimental results suggest Said parameter describes empirically that, with a change in the absorbed intensity, beam hardening occurs and thus also a changed penetration depth into the detector material in the area surrounding the corresponding pixel. The same also applies for the displacement of the source location. This leads to a changed local enlargement at this point and thus to a displacement of the intensity from this pixel to adjacent pixels. The parameters k and c can be assumed to be different for different areas of the image if different test object materials contribute to absorption in said areas.

The above formula applies for the radially symmetrical case brought about by the displacement of the detector location 5. With regards to the displacement of the source location, if the source location shifts with one vector component along a tilted target parallel to the detector, this symmetry is broken. This can be taken into account by ensuring an additional pixel-by-pixel displacement in the Y direction (towards a target inclination as shown in FIG. 1). However, this is approximately independent from the Y position on the detector, but proportional to the absorbed intensity: $\Delta r=(I_0-I)*w$, wherein w is a constant with similar dependencies as k.

The correction of the influence of the penetration depth is preferably conducted such that a differential distance between the zero point distance of the corrected position and the zero point distance of the uncorrected position is generally calculated from a product of the intensity measured by the respective pixel and an intensity parameter. This intensity correction parameter is preferably a constant, in particular the intensity correction parameter does not depend on the zero point distance, at least in a linear order of the zero point distance. Specifically, the intensity correction parameter is also not dependent on the intensity.

The characteristic that the differential distance is generally calculated in the way given above should be understood particularly to mean that it is possible but not necessary for further parameters to be included in the calculation of the differential distance. Any additional input that is not the product of intensity and intensity correction parameter is preferably smaller than one third, especially smaller than one fifth, of the product of intensity and intensity correction parameter.

The X-ray radiation is preferably generated by irradiating a source point of a target with electrons. The calculation of the dimensions of the test object is preferably achieved by way of an enlargement factor, which is calculated from the quotients of the distance b of the source point from the detector and a distance a of the test object from the source point. The enlargement factor is preferably corrected by the influence of an electron penetration depth into the target. This is achieved, for example, by correspondingly calculating the differential distance in the same way as described above. In other words, the calculation given above can be utilised to compensate both the influence of the penetration depth in the detector and the effect of a displacement of the effective source point caused by beam hardening.

The enlargement factor is preferably determined by measuring a—preferably thinner—calibration body with known dimensions. This is conducted in accordance with the steps (a) to (c) according to claim 1. The thickness of the (pre) filter, with which the X-ray beam is filtered, is then changed before it strikes the calibration body and measured once again. The intensity correction parameter is then calculated from a change in the enlargement of the shadow image of the calibration body on the detector, depending on the intensity of the X-ray radiation. A change of filter strength of the filter effects a change in the intensity that is measured at a given pixel; the X-ray spectrum also changes.

The exact displacements of the source location and detector location can be determined as follows, which enables the calculation of c and v: at least four measurements must be made at different measured geometric enlargements V1 to V4 with different positions of the calibration body under otherwise equal conditions, so that the displacements of the source location ($\tau_e$)—and the detector ($\delta$) can be separated. This results in a system of equations:

$$V1=(b+\delta+\tau_e)/(a+\tau_e)$$

$$V2=(b+d1+\delta+\tau_e)/(a+d1+\tau_e)$$

$$V3=(b+d2+\delta+\tau_e)/(a+d2+\tau_e T)$$

$$V4=(b+d3+\delta+\tau_e)/(a+d3+\tau_e)$$

Measurements taken at different positions are beneficial as the overdetermination of the equation system allows for the calculation of statistically more accurate results. d1 to d3 represent displacements of the test object in relation to the starting position, which can preferably be determined by means of a laser interferometer.

The experimentally determined enlargements V1 to V4 are calculated as the quotient of the size of the image on the detector 14 and the known dimensions of the calibration body. The size of the image on the detector is calculated from the dimensions of the image in pixels multiplied by the known distance of two pixels. In order to compensate for the offset of the calibration body from the rotational axis, the measurements can be repeated at the 0° and 180° position of the axis and a mean value calculated. It is preferable if a uniform lattice structure can be used as a calibration body, the lattice constant of which is used as a material measure.

a, b, $\delta$ and $\tau_e$ are therefore unknown variables that can be determined using the equation system of four equations. Once the parameters are known, the parameter c required to correct the image at the given enlargement can be calculated. Typical values of c for the preferred parameters, already described above, of the tomography scanners are 100 μm to 300 μm, which effect a change in the enlargement by a relative amount of $1\cdot 10^{-4}$ to $3\cdot 10^{-4}$, for example at a distance of one meter from detector to source. By using different, preferably thinner, calibration bodies made of different material and under different conditions of the beam source, relative changes of c can be determined by comparing the geometric enlargement factors when the geometric relations otherwise remain the same. This renders the measurement in different positions unnecessary for the determination of c for other operating conditions and test object materials.

It is beneficial if, during the measurement of a test object that is not a calibration body, a filter is used which filters out a maximum of 75% of the total intensity of the raw radiation. This results in a particularly low measuring time. At the same time, this requires a broad X-ray spectrum which leads to particularly high deviations without the correction of the radiographic images according to the invention. Conversely, this means that the application of the method according to the invention enables a lower degree of filtering and therefore shorter measuring times, which is an economic benefit.

In the following, the invention will be explained in more detail by way of the attached drawings. They show FIG. 1 a schematic depiction of an X-ray computed tomography scanner according to the invention for conducting a method according to the invention, FIG. 2 by way of the partial FIGS. 2a and 2b, a schematic depiction of how the pixel-dependent intensity data is corrected by the factor to compensate for the influence of the penetration depth, and FIG. 3 by way of the partial FIGS. 3a and 3b, experimental data in which the dependency of the enlargement on the absorbed intensity is shown.

FIG. 1 shows a schematic view of an X-ray computed tomography scanner 10 according to the invention which comprises an X-ray source 12 and a detector 14. The X-ray source 12 has an electron beam source 16 for generating an electron beam 18, which is directed at a target 20. The target 20 is made of tungsten, for example. The electrons of the electron beam 18 have an energy of 225 kilo electronvolts, for example. The electron beam 18 strikes the target 20 at a source point Q. An angle of impact between the electron beam 18 and a surface of the target 20 preferably lies between 15 and 30°. Alternatively, a thin target can may also be penetrated from behind.

When the electrons of the electron beam 18 strike the target 20, X-ray radiation occurs, which, for the purposes of a simplified assessment, can be considered to be made up of several X-ray beams 22.$i$. The drawing shows two beam paths with the index i=1, 2. An optical filter 24 is arranged in the beam direction behind the target 20, said filter effecting beam hardening of the X-ray beams 22.$i$. The filter is made of aluminium or copper, for instance, and has a thickness d.

A test object 26 is arranged in the beam path behind the filter 24. The test object 26 comprises a structure 28 that is to be measured, such as a bore, and the material 30 surrounding the structure 28. This imagined division of the test object 26 into structure 28 and material 30 only serves to explain the invention and should not contain any restrictive statements on the type of test object.

The X-ray computed tomography scanner 10 preferably features a test specimen accommodation for accommodating the test object 26. The test specimen accommodation is preferably designed as a movement device 32, especially a rotation device for rotating the test object 26 about a rotational axis D. The rotational axis D is at a first distance a from the source point Q.

The detector 14 is arranged in the beam direction behind the test object 26 and is at a second distance b from the source point. In the present case, the detector 14 features a scintillator element 34, which has a plurality of microcolumns 36. The microcolumns extend perpendicular to a detector plane E and are made of cesium iodide crystallite needles, for example. If an X-ray quantum strikes the detector 14, a flash of light appears, which then spreads along the adjacent microcolumns, thereby striking a small number of photovoltaic cells. It should be noted that the running Index I is used for several objects without it specifically referring to an assignment of said objects with respect to each other.

FIG. 1 depicts two scenarios for a shadow image S, S' of the test object 26 on the detector 14. For the first scenario, two X-ray beams 22.1', 22.2' are depicted with a dashed line leaving the source point Q'; this corresponds to the case in which no filter 24 is present and the test object 26 is made up solely of the structure 28. This results in minimal beam hardening and a higher intensity, which is measured by the detector 14. Due to the low degree of beam hardening, the effective penetration depth τ' is comparatively small. For the second scenario, two X-ray beams are depicted by a solid line, said beams passing through the same pairs of points P1 and P2 of the structure, wherein a filter 24 is available and/or the structure 28 is surrounded by a significant amount of material 30. As detailed in the introduction to the description, beam hardening occurs and thus also a greater effective penetration depth T into the detector 14. The difference δ=τ−τ' is greater than zero. The path from the source to the detector b thus increases by this value and, at a ratio (b+δ)/b, the depiction of the points P1 and P2 lies further apart than in the original image. A second impact of the additional beam hardening effected by the absorber 30 is that the average source location Q on the target is different. Given that the target runs diagonally to the axis A, the distances a and b enlarge simultaneously by the value $\tau_e$; a lateral offset occurs, which strikes in a geometrically enlarged form as offset E in the image in the direction of the target tilt. The measurement results of the detector 14 are evaluated by means of an evaluation unit 40, which comprises at least processor and a digital memory for this specific purpose.

Figure 2:
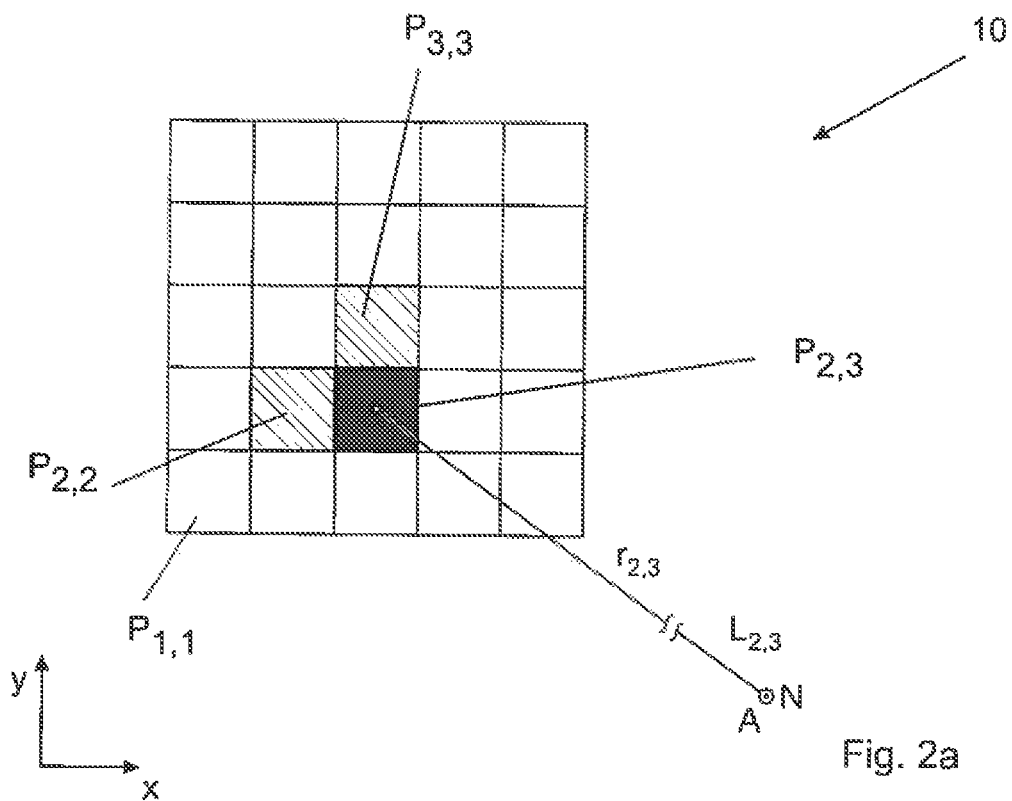
Figure 2:
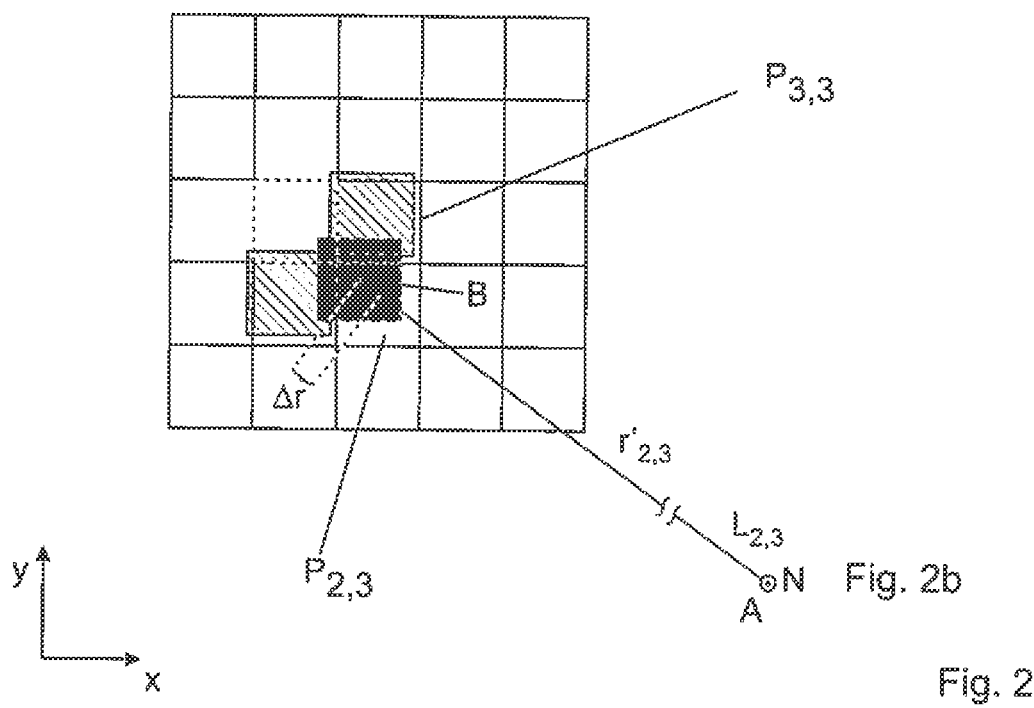

FIG. 2$a$ shows how the described effect can be corrected and schematically depicts a section of the detector 14 with the pixels $P_{x,y}$. The pixel $P_{2,3}$ detects a very low intensity $I_{2,3}=I(P_{2,3})$. Conversely, the pixels $P_{3,3}$ and $P_{2,2}$ detect a median intensity $I_{3,3}$ or $I_{2,2}$. For the remaining pixels P, it is assumed that, for the sake of simplicity, they detect a maximum intensity $I_{x,y}=I_{max}$.

The pixel $P_{2,3}$ has a zero point distance $r_{2,3}$ from a zero point N (see FIG. 1) of the detector 14 on the optical axis (see FIG. 1). The optical axis A is the line that runs through the source point Q and stands perpendicular to the detector plane E along which the detector 14 extends. Approximately, the source point is used that is detected when neither a filter nor a test object is present in the structure.

FIG. 2$b$ shows that the pixel-dependent intensity data can be corrected by the influence of the penetration depth τ and the source location displacement $\tau_e$ by allocating the intensity $I(P_{2,3})$, i.e. the intensity measured by the pixel $P_{2,3}$, a new position K. This new position K is calculated by way of the displacement lattice of the position of the original pixel $P_{2,3}$ in the direction of the connection line $L_2$ from the optical axis A to the original position of the pixel $P_{2,3}$. The new distance $r'_{2,3}$ is calculated as $r'_{2,3}=r_{2,3}(1+k\cdot i_{2,3}+c)$ with the displacement parameter k, the material-dependent constant c and the intensity I. For the sake of simplicity, it is assumed here that c=0.

As schematically depicted in FIG. 2$b$, this corresponds to an imagined displacement of the position of the pixel $P_{2,3}$ relative to the original pixel pattern and thus the original coordinate system. In the same way, the corresponding displacement is calculated for all pixels $P_{x,y}$. This is implied for the pixels $P_{3,3}$ and $P_{2,2}$.

In a subsequent step, each pixel $P_{x,y}$ is allocated a corrected intensity $I'_{x,y}$. This is achieved by calculating for each pixel what proportion of the surface of the respective pixel exhibits the calculated displaced intensity. In this way, the intensity $I'_{2,3}$ is allocated to the pixel $P_{2,3}$, which in the present case corresponds to 0.52-times the intensity $I_{2,3}$, given that only 52% of the black surface lies in the region of the pixel $P_{2,3}$, which can be seen in FIG. 2$b$. This area B is circled with a dot-dash line in FIG. 2$b$. The intensity $I'_{3,3}$, which is allocated to the pixel $P_{3,3}$, is $I'_{3,3}=I_{2,3}\cdot 0,22+0,82\cdot I_{33}$. This calculation is conducted for all pixels $P_{x,y}$ of the original image of the detector 14. The intensity data that is corrected in this manner produces a corrected image of the detector 14 and is then used to reconstruct a three-dimensional density image of the test object 26.

It should be noted that it is beneficial, but not necessary, to calculate the intensities for the original pixel pattern. It is also conceivable and included in the invention that this pixel-by-pixel intensity correction, which redistributes intensity to other adjacent pixels, be applied for a different pixel pattern, such as hexagonal lattice.

FIG. 1 shows that an enlargement factor V=b/a can be calculated from the first distance a and the second distance b, said enlargement factor indicating how much larger the shadow image S, S' appears on the detector 14 in relation to the structure 28. In order to measure a dimension, such as a height H of a recess in the test object 26, this enlargement factor V must be known. The enlargement factors V1 to V4 and the distances a and b are explained above. The enlargement is an indirect measured value if the dimensions of the calibration lattice are known and the pixel distances of the detector are assumed to be known (e.g. 200 μm). Firstly, these are very well-known and secondly, the detector pixel sizes are no longer included in the results, as all dimensions are measured in pixels/voxels and considered in relation to the calibration object.

Figure 3A:
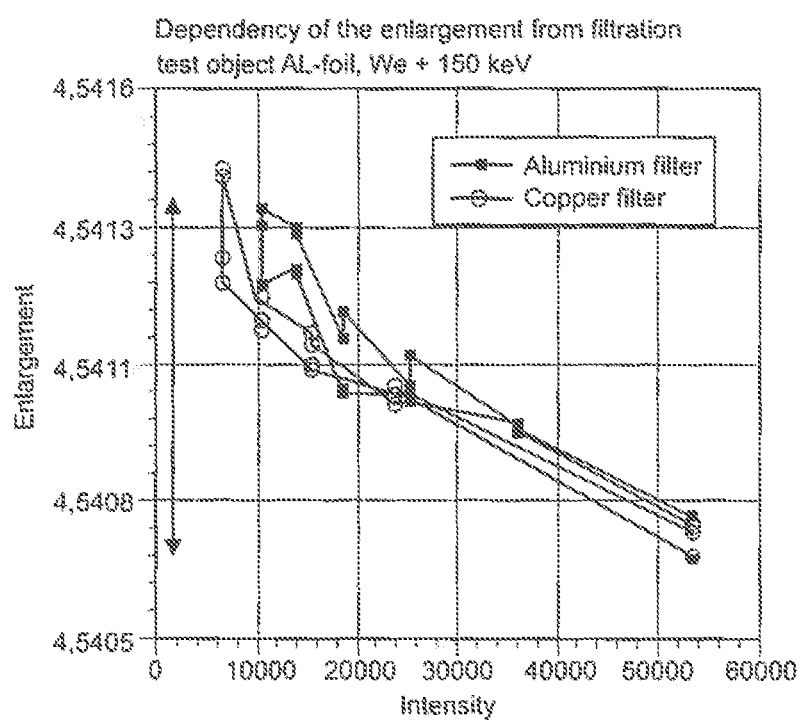

The X-axis in FIG. 3a is the intensity I measured by the detector. The intensity is changed by way of increasingly thicker pre-filters made of either copper (circles) or aluminium (squares). The test object 26 consists solely of a structure 28 in the form of an aluminium foil with several recesses, which are arranged at known positions. The Y-axis indicates the enlargement factor V. It should be noted that the enlargement factor V decreases with increasing intensity I or increases with stronger absorption. The reason for this change is the above-described influence of the increasing beam hardening on the penetration depth and the apparent position of the source point.

Figure 3B:
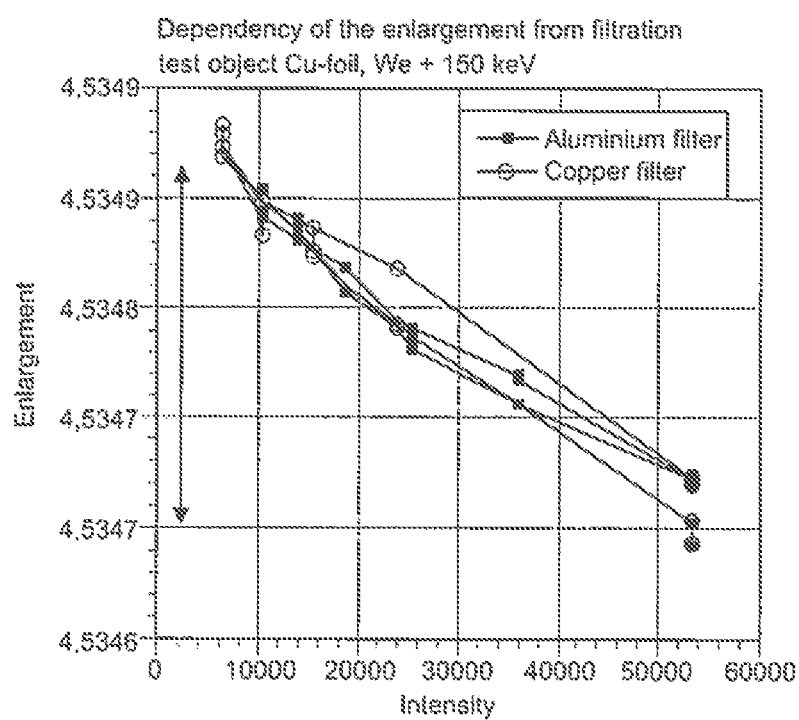

As in FIG. 3a, FIG. 3b depicts a diagram, wherein the test object 26 consists solely of a structure 28 in the form of a copper foil with several recesses, which are arranged at known positions.

| Reference list | |
|---|---|
| 10 | X-ray computed tomography scanner |
| 12 | X-ray source |
| 14 | detector |
| 16 | electron beam source |
| 18 | electron beam |
| 20 | target |
| 22 | X-ray beam |
| 24 | filter |
| 26 | test object |
| 28 | structure |
| 30 | material |
| 32 | test specimen accommodation, rotation device |
| 34 | scintillator element |
| 36 | micro-columns |
| 38 | photovoltaic element |
| 40 | evaluation unit |
| a | first distance |
| A | optical axis |
| b | second distance |
| d | filter strength |
| D | rotational axis |
| E | detector plane |
| H | height |
| I | intensity |
| K | position |
| L | distance to centre of image |
| P | pixel |
| Q | source point |
| r | distance |
| S | shadow image |
| k | intensity correction parameter |
| V | enlargement factor |
| w | constant |
| δ | difference |
| ε | displacement |
| τ | effective penetration depth |
| $τ_e$ | effective source point Displacement |

The invention claimed is:

1. A method for dimensional X-ray measurement, comprising:
   (a) irradiating a test object with non-monochromatic X-ray radiation from a virtually punctiform X-ray source,
   (b) measuring an intensity of the X-ray radiation in a radiation path behind the test object by a flat detector which has a plurality of pixels to obtain pixel-dependent intensity data, and
   (c) calculating at least one dimension of the test object using the pixel-dependent intensity data,
   (d) correcting the pixel-dependent intensity data based on an effective penetration depth change on the flat detector due to beam hardening and/or a displacement of an effective source location change on a target of the X-ray source due to beam hardening.

2. The method according to claim 1 wherein the X-ray radiation is generated by irradiating a source point of a target with electrons,
   (i) calculation of dimensions of the test object is executed using an enlargement factor, which depends on
      a distance of the source point from the detector and
      a distance of the source point from the test object, and that
   (ii) the enlargement factor is corrected based on an X-ray emission spectrum that changes due to a changing electron penetration depth into the target.

3. The method according to claim 1 wherein
   the X-ray radiation is generated by irradiating a source point of a target with electrons such that raw radiation occurs, and
   further comprising filtering of the raw radiation by a filter, said filter filtering out a maximum of 75% of a total intensity of the raw radiation.

4. An X-ray computed tomography scanner, comprising:
   (a) an X-ray source for generating X-ray radiation,
   (b) a detector, which features a plurality of pixels, for measuring pixel-dependent intensity data of the X-ray radiation,
   (c) a movement device for moving a test object relative to the X-ray source and the detector, and
   (d) an evaluation unit for calculating a three-dimensional image of the test object using the pixel-dependent intensity data,
   wherein the evaluation unit is designed to automatically execute a method according to claim 1.

5. The X-ray computed tomography scanner according to claim 4, wherein the evaluation unit is designed to automatically execute a method containing the steps:
   correcting pixel-dependent intensity data based on a penetration depth on the detector and/or a displacement of the effective source location on a target of the X-ray source, such that corrected pixel-dependent intensity data is obtained, and
   calculating the three-dimensional image using the corrected pixel-dependent intensity data.

6. The X-ray computed tomography scanner of claim 4 wherein the movement device is a rotation device.

7. A method for dimensional X-ray measurement, comprising:
   (a) irradiating a test object with non-monochromatic X-ray radiation from a virtually punctiform X-ray source,
   (b) measuring an intensity of the X-ray radiation in a radiation path behind the test object by a flat detector which has a plurality of pixels to obtain pixel-dependent intensity data, and
   (c) calculating at least one dimension of the test object using the pixel-dependent intensity data,
   (d) correcting the pixel-dependent intensity data based on an effective penetration depth on the flat detector and/or a displacement of an effective source location on a target of the X-ray source wherein
   the pixel-dependent intensity data is corrected by a change in the effective penetration depth on the detector, said change being caused by beam hardening.

8. A method for dimensional X-ray measurement, comprising:
   (a) irradiating a test object with non-monochromatic X-ray radiation from a virtually punctiform X-ray source,
   (b) measuring an intensity of the X-ray radiation in a radiation path behind the test object by a flat detector which has a plurality of pixels to obtain pixel-dependent intensity data, and
   (c) calculating at least one dimension of the test object using the pixel-dependent intensity data,
   (d) correcting the pixel-dependent intensity data based on an effective penetration depth on the flat detector and/or a displacement of an effective source location on a target of the X-ray source, wherein
   the pixel-dependent intensity data is corrected by a displacement of the effective source location on the target of the X-ray source, said change being caused by beam hardening.

9. A method for dimensional X-ray measurement, comprising:
   (a) irradiating a test object with non-monochromatic X-ray radiation from a virtually punctiform X-ray source,
   (b) measuring an intensity of the X-ray radiation in a radiation path behind the test object by a detector which has a plurality of pixels to obtain pixel-dependent intensity data, and
   (c) calculating at least one dimension of the test object using the pixel-dependent intensity data,
   (d) correcting the pixel-dependent intensity data based on an effective penetration depth on the detector and/or a displacement of an effective source location on a target of the X-ray source, wherein
   the correction by a change in the effective penetration depth comprises the following steps:
   for at least a majority of the pixels
   (i) identifying a zero point distance of a pixel from an optical axis,
   (ii) identifying an intensity of the X-ray radiation measured by the pixel,
   (iii) allocating a corrected position depending on the zero point distance and the intensity for the pixel, and
   (iv) calculating corrected pixel-dependent intensity data from all corrected positions and the corresponding intensities.

10. The method according to claim 9, wherein
    a corrected position and a zero point distance of an original position lie on one line.

11. The method according to claim 9 wherein
    a differential distance between the zero point distance of a corrected position and a zero point distance of an original position is calculated from a term which contains a product of a function of the intensity, an intensity correction parameter and a constant.

12. The method according to claim 11, comprising:
    measuring a test object in the form of a calibration body,
    changing a filter strength of a filter, and
    calculating an intensity correction parameter from a displacement of a shadow image of the test object on the detector, depending on the intensity of the X-ray radiation.

* * * * *